United States Patent [19]

Renirie et al.

[11] Patent Number: 5,458,624
[45] Date of Patent: Oct. 17, 1995

[54] CARDIAC PACING SYSTEM WITH IMPROVED END-OF-LIFE DETECTOR

[75] Inventors: W. C. M. Renirie, Berg en Dal; Andrei Tudose, Hengelo; B. F. M. Vonk, Wehl, all of Netherlands

[73] Assignee: Vitatron Medical, B.V., Dieren, Netherlands

[21] Appl. No.: 132,713

[22] Filed: Oct. 6, 1993

[51] Int. Cl.⁶ ............................................. A61N 1/37
[52] U.S. Cl. ............................................. 607/29
[58] Field of Search ............................... 607/27, 29

[56] References Cited

U.S. PATENT DOCUMENTS 4,290,429  9/1981  Blaser.
4,556,061  12/1985  Barreras et al..
4,715,381  12/1987  Moberg.
5,137,020  8/1992  Wayne.

Primary Examiner—William E. Kamm
Assistant Examiner—Scott M. Getzow
Attorney, Agent, or Firm—Woodcock Washburn Kurtz Mackiewicz & Norris

[57] ABSTRACT

A pacemaker is provided having an improved circuit for obtaining a measure of battery end-of-life. The EOL detector includes an input stage with a current mirror output providing a current which is proportional to the current being consumed by the pacemaker circuitry, and thus being expended by the battery. The proportional current is directed to charge a capacitor, which is periodically discharged at a constant current, following which the battery goes through repeated cycles of charging and discharging. A measuring circuit measures the time of capacitor discharge, thereby providing a measure of battery energy discharge during the interval that the capacitor was charging. The interval counts are accumulated to provide an overall count representative of battery expenditure, and thus of pacemaker EOL.

17 Claims, 4 Drawing Sheets

CARDIAC PACING SYSTEM WITH IMPROVED END-OF-LIFE DETECTOR

BACKGROUND OF THE INVENTION

1. Field of the Invention

The present invention relates to cardiac pacemakers and, more particularly, to cardiac pacemakers with the facility to continuously detect a measure of battery expenditure so as to predict nominal pacemaker end-of-life (EOL).

2. Description of the Prior Art

In the area of implantable cardiac pacemakers, it has long been recognized that it is important to have the capacity to determine a measure of the effective remaining lifetime of the implanted pacemaker. Although great improvements have been made in the batteries that are used in pacemakers, extending significantly the available lifetime of pacemakers, there remains a need to have accurate information from which to predict EOL. As used herein, and as is common in the pacemaker art, end-of-life refers to a time when the battery has been drained sufficiently that the pacemaker should be replaced. Thus, EOL generally does not refer to a time when a pacemaker actually ceases to operate effectively, but a time by which the pacemaker should be replaced while there is still a sufficient factor of safety. Thus, e.g., the pacemaker manufacturer may recommend a replacement of the pacemaker at a time when it actually has an estimated three months of lifetime remaining, to guarantee that replacement takes place before there is a significant danger of actual cessation of pacemaker operation.

An early technique for EOL detection in pacemakers was founded upon the characteristics of the battery impedance. Based upon the observation that battery internal impedance was substantially constant throughout most of the battery lifetime, and then began to increase as battery exhaustion approached, the standard technique utilized was to isolate the battery from the pacemaker briefly in order to get an internal impedance measurement. See, for example, U.S. Pat. No. 5,137,020, assigned to Medtronic, Inc. However, in the latest generation of batteries utilized in implantable pacemakers, the impedance change occurs too quickly to provide sufficient warning, and cannot be reliably detected safely in advance of effective battery exhaustion. Consequently, another engineering approach to the matter is required.

The more recent solution to the problem of measuring EOL in the pacemaker art is based on the fact that the battery energy at start-of-life is accurately known. The pacemaker is provided with a circuit for obtaining a measure of total, or integrated battery current expenditure, and determining from this measure what percentage of battery energy has been depleted. By making it possible for a physician to determine what percentage of the battery capacity has been expended, the physician can project a remaining safe lifetime. The basic concept of detecting EOL by accumulating a measure of energy usage in an implanted pacemaker is illustrated in U.S. Pat. Nos. 4,556,061 and 4,715,381. In U.S. Pat. No. 4,556,061, there is provided a battery consumption monitor circuit which develops with an internal counter a cumulative count representative of energy consumption by the pacemaker. A sense resistor is used to develop a voltage representative of pacemaker current flow, which voltage is imposed upon a voltage-controlled oscillator (VCO), the output of which is inputted into the internal counter. The counter continuously accumulates the pulses so as to provide a measure of the integral of battery current flow, and thus total energy expenditure. However, the accuracy of the VCO is a function of its capacitor, such that the use of VCO in this manner makes the EOL detector capacitor-dependent. It is very difficult and expensive to provide an extremely precise capacitor value for an implantable pacemaker application. Further, the expected variability of the capacitor value over the lifetime of an implanted pacemaker, which may be up to ten or more years, leads to a loss of accuracy. Accordingly, what is needed is a more reliable form of detecting battery consumption and, in particular, an EOL detector which is not capacitor-dependent. Optimally, what is desired is an EOL circuit where, to the extent any capacitor is utilized, the capacitor can change in value over the life of the pacer and not affect the accuracy of the measurement, i.e., the EOL detector is capacitor-independent and otherwise highly reliable.

U.S. Pat. No. 4,715,381 illustrates a technique of making calculations of approximate battery energy expenditure, rather than actually measuring battery consumption. This reference shows a stimulation pulse counter which counts the number of delivered stimulus pulses. This information is utilized together with the programming parameters to determine the total amount of energy of the delivered pulses over an elapsed time. This calculated signal is added to a fundamental consumption signal which is based upon certain approximations and assumptions, and used to derive a signal representative of approximate total battery expenditure. This technique clearly provides at best an approximation, and is inherently subject to a greater probability of inaccuracy than the energy consumption technique. Further, neither of the prior art techniques are as energy efficient as desired, i.e., the EOL detector itself involves counters, oscillators and the like which are constantly operating and consume an undesirable amount of energy. Thus, there remains a substantial need in the pacemaker art for an improved EOL detector which is more reliable and accurate, can be built with minimum cost, and which itself draws an optimally minimum amount of energy from the pacemaker battery.

SUMMARY OF THE INVENTION

In accordance with the above-described need in the art, there is provided an implantable pacemaker system with an improved EOL detector with a reliable circuit for measuring pacemaker consumption, and means for projecting EOL in the implanted pacemaker. The detector provides an effectively capacitor-independent circuit for providing an accurate measure of total energy expenditure from the battery. The system further provides for an automatic calculation of remaining battery life and thus of anticipated EOL. The EOL detector comprises a circuit for accumulating a signal representative of recent energy consumption, which signal is obtained by accumulating on a capacitor a signal representative of the integral of pacemaker current with time since the initiation of the last accumulation on the capacitor. This signal is read when the capacitor voltage reaches a trigger threshold, the signal reading being accomplished by generating pulses representative of the accumulated charge being discharged from the capacitor. An accurate reading is made by discharging the capacitor at a fixed discharge current over the time of current discharge, and generating a number of pulses proportional to the time of discharge. The pulses, which represent energy consumed by the pacemaker while the capacitor was charging, are accumulated in a counter. Following discharge or zeroing out of the capacitor, the accumulation of the running measure of battery expenditure is repeated, following which another readout takes place. The EOL detector thus cycles through the steps of reading out a measure of energy consumption since the last reading, accumulating the measure of energy consumption, and repeating these steps. The technique of timing a constant current discharge from the capacitor provides a measure which is substantially independent of capacitor variation, thereby providing an improved EOL detector with greater accuracy and reliability.

DESCRIPTION OF THE PREFERRED EMBODIMENTS

Referring now to the figures, the preferred embodiment of this invention is described. As used in the claims appended hereto, the term EOL detector, or simply detector, may comprise either a circuit for obtaining a measure of battery energy expenditure, or apparatus which both obtains a measure of battery energy expenditure and provides an indication of remaining lifetime.

Figure 1:
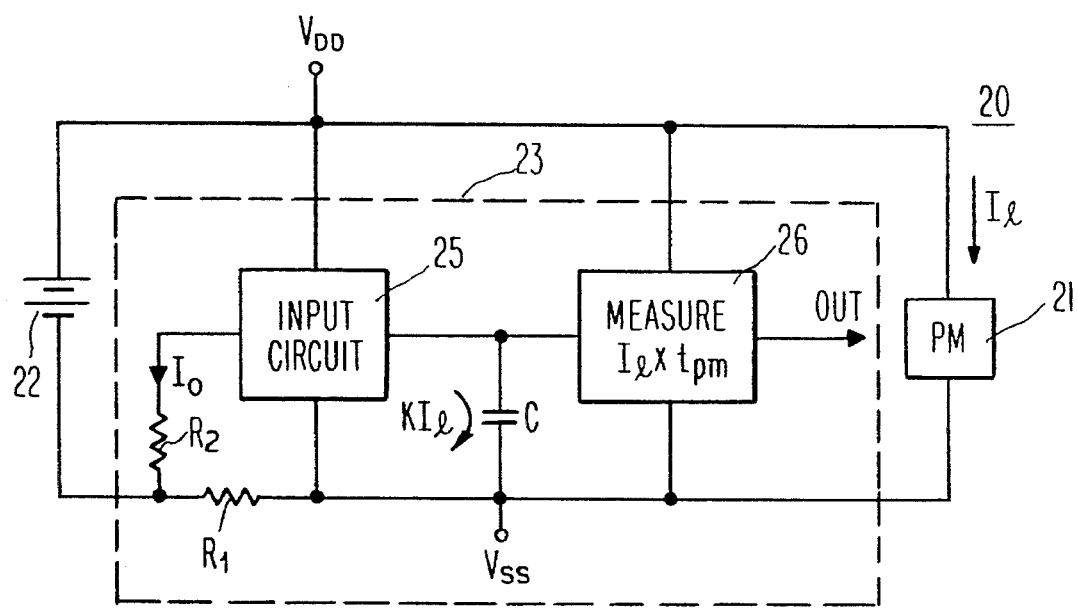
FIG. 1 is a block diagram showing the basic circuit components of an implantable pacemaker with a preferred embodiment of the improved EOL detector of this invention.

Referring now to FIG. 1, there is shown a simplified block diagram representing the basic components of a pacemaker 20 having an improved EOL detector. The pacemaker has pacemaker circuitry 21, which comprises all circuitry, both hardware and software, within the implanted pacemaker, except for the EOL detector circuitry. Thus, pacemaker circuitry 21 comprises one or more generators for generating stimulus pulses, hardware and/or software for performing logic functions and making decisions as to when and when not to deliver stimulus pulses, and all other functions that are well known in the pacemaker art. Pacemaker circuitry block 21 may also embrace leads for delivering stimulus pulses to a patient's heart and for receiving therefrom signals representative of natural heartbeats. The current through pacemaker circuitry 21 is designated as $I_l$. The pacemaker also comprises a battery 22, which provides power to the pacemaker.

The detector circuit indicated at 23 comprises an input circuit 25 designed to output a current proportional to $I_l$, namely a current indicated as $KI_l$. A sense resistor $R_1$ develops thereacross a voltage proportional to $I_l$. A second resistor, indicated as $R_2$ is connected at one end to a node between battery 22 and resistor $R_1$ and at its other end to an input to circuit 25. The other end of resistor $R_1$ is also connected as a second input to circuit 25. As is explained further in connection with FIG. 3, the sense current ($I_s$) through resistor $R_2$ equals approximately $R_1/R_2 \times I_l$. Circuit 25 provides an output current proportional to the input current, such that $I_{out}$ flows into and charges capacitor C. Block 26 is a circuit which repeatedly discharges capacitor C and, upon each such discharge, obtains a measure of the pacemaker circuit current times the time that the current has flown, i.e., $I_l \times t_{pm}$, which in turn is a measure of the energy discharge from the battery during the time of charging the capacitor. Each such measure corresponding to each such capacitor discharge is added, or accumulated, to obtain an overall measure of $I_l \times t_{pm}$, representing overall battery discharge. The overall measure can be accessed through an external interrogating device, in a well known manner.

Figure 2:
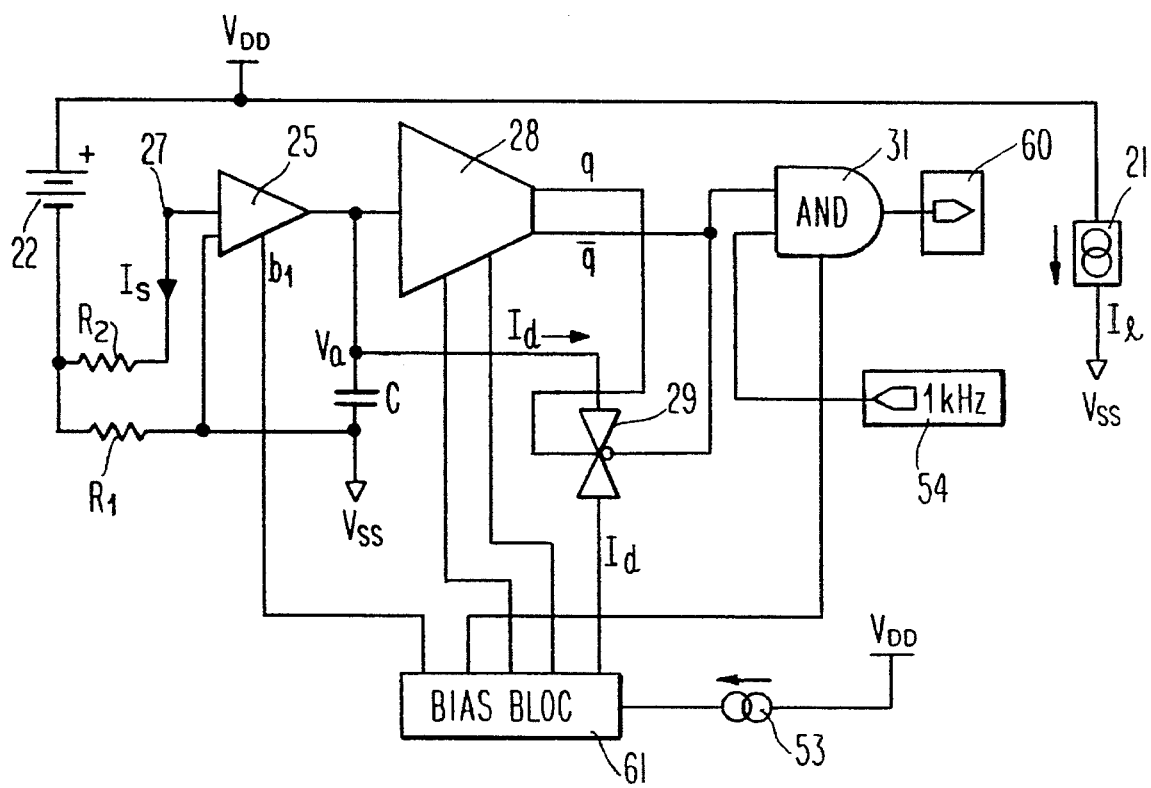
FIG. 2 is a more detailed circuit diagram of the pacemaker of this invention with the improved EOL detector.

Referring now to FIG. 2, there is shown a more detailed circuit diagram of the pacemaker of this invention with an improved EOL detector. Resistor $R_1$, across which $I_l$ flows, is selected as approximately 1K. As is appreciated by those knowledgeable in the circuit arts, the choice of $R_1$ is a compromise between obtaining accuracy, minimizing power dissipation, and reducing the voltage drop across $R_1$. The choice of about 1K ohms is made to optimize these factors. The value of $R_2$ is chosen as approximately $10^6$, or 1 Meg. The input current $I_s$, shown at node 27 connected to input circuit 25, is proportional to $I_l$ by a factor K, where K is the ratio of $R_1$ to $R_2$. As seen also in FIG. 3, where circuit 25 comprises an operational amplifier, $I_s = R_1/R_2 \times I_l$. The input stage is further designed to provide an output charging current for the capacitor C of the same value, i.e., $R_1/R_2 \times I_l$. Thus, assuming initially no charge on capacitor C, the voltage at the node designated $V_a$ accumulates in accordance with the integral of $I_l$ with time. When $V_a$ reaches a positive Schmitt trigger threshold voltage, $V_{th+}$, the output from the Schmitt trigger 28 closes analog gate 29. A fixed discharge current $I_d$, provided by a bias block 61, discharges capacitor C until $V_a$ reaches $V_{th-}$ (a negative Schmitt trigger threshold voltage). At this moment, gate 29 is switched off and the voltage $V_a$ begins to increase again. This procedure of discharging the capacitor to $V_{th-}$ and then starting a new cycle of charging, is referred to as zeroing out the accumulated voltage signal.

It is seen that the time that it takes to discharge capacitor C with the programmed current value $I_d$, enables a determination of the accumulated charge on capacitor C, which in turn represents a measure of the energy expended by the battery 22. The energy, or amp hours (Ah) is obtained from the following expressions:

$$I_l \div R_1/R_2 \times t_{pm} = I_d \times t_d$$

where $t_{pm}$ is the time during which the pacemaker has been operating, $I_l$ is the instantaneous line current value (μA), $t_d$ is the period during which the capacitor is discharged, and $I_d$ is the capacitor C discharging current set by the bias block 61. For example, $I_d$ may be in the range of about 200 nA to 1000 nA.

Consequently:

$$I_l \times t_{pm} = k \times t_d,$$

where k depends upon the values of $R_2$, $R_1$ and $I_d$. AND gate 31 is connected to receive a first input from the Schmitt trigger 28 and a second input from a 1 KHz generator 54. During discharge, the Schmitt trigger output enables clock pulses to pass through the AND gate, which pulses are then counted in counter 60. The number of pulses delivered to the counter while the capacitor is discharging is a measure of $t_d$, and therefore of $I_l \times t_{pm}$.

As seen from the last equation above, the measure of current consumption provided by this circuit is effectively independent of the value of the capacitor C. If the capacitance varies, this results in a change in the accumulated charge before $V_{th+}$ is reached. But, by discharging the capacitor with the fixed current $I_d$, the count of the 1 KHz pulses is always proportional to the charge withdrawn from the capacitor, and thus to current consumption. As long as the capacitor has a value such that the time of discharge $(t_d)$ is large compared to the 1 ms period between the 1 KHz pulses, the accuracy is effectively independent of variations in the value of C. The pulse rate of 1 KHz is a compromise between current consumption and accuracy. Other rates can be used, e.g., between about 500 Hz and 5000 Hz.

It is to be noted that the mechanism of counting the discharge time by counting pulses does introduce some error. For a 1 KHz signal, the quanta or period of 1 ms. There is a theoretical start counting error induced by the time offset between the rising edge of the 1 KHz signal and the rising signal of the Schmitt trigger output signal. Likewise, there is a stop counting error due to the time offset between the falling edge of the 1 KHz signal and the falling edge of the Schmitt trigger output signal. While a higher pulse rate would lead to less error and greater accuracy, such a higher rate would require a counter with greater capacity to count the increased number of pulses. Since a high capacity counter is not desirable for an implantable device, in the preferred embodiment a 1 KHz signal is used and the value of the capacitor C is selected so that accuracy is maintained within a predetermined tolerance.

The counting mechanism is a measure of the capacitor discharge time. If it is assumed that the Schmitt trigger has a threshold hysteresis, or voltage window of 1 V, and the discharge current is 1000 nA, then:

$$t_d = \frac{\Delta V_{th} \cdot C}{I_d}$$

In order to achieve an accuracy of 0.5% or greater in view of the count mechanism induced error, the minimum discharge period is 100 ms. This would yield a capacitance value of 100 nF. For a shorter discharge window, e.g., 0.75 v, a proportionately greater capacitance value is used. To be safely within the 0.5% error tolerance, a capacitance value in the range of 100–200 nF is appropriate.

It is to be noted that a simpler embodiment of the invention can be obtained at some sacrifice of accuracy. In such a case, the 1 KHz generator 54 and the AND gate 31 are eliminated, and only the signal changes from the output of circuit 28 are counted. This gives a good result, but not as good as the preferred embodiment, since changes in C or $V_{th+}$ and $V_{th-}$ affect accuracy.

In practice, the bias block provides an analog bias current to input stage 28; an analog bias voltage to Schmitt trigger 28; a digital bias voltage to Schmitt trigger 28; a discharge current to gate 29; and a digital bias current to AND gate 31. The bias block starts with a 20 nA reference 53 from pacemaker circuitry 21 and builds separate current sources therefrom. A modified cascode current mirror is suitable for providing $I_d$.

Figure 3:
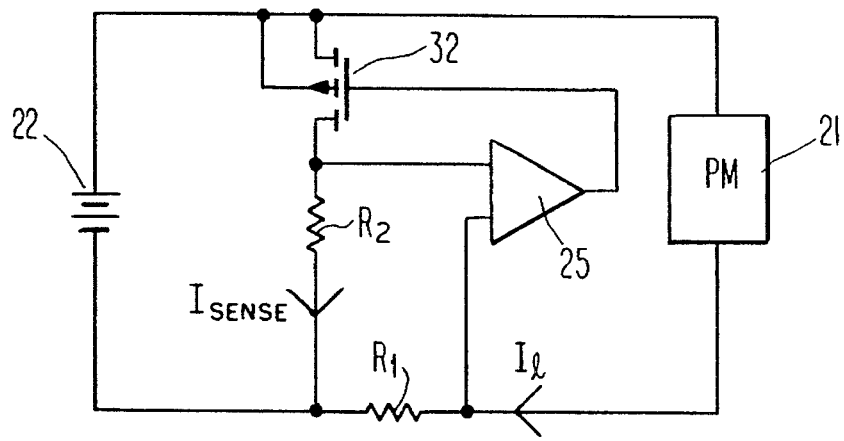
FIG. 3 is a simplified circuit diagram showing the feedback configuration for obtaining an input signal representative of pacemaker current.
Figure 4:
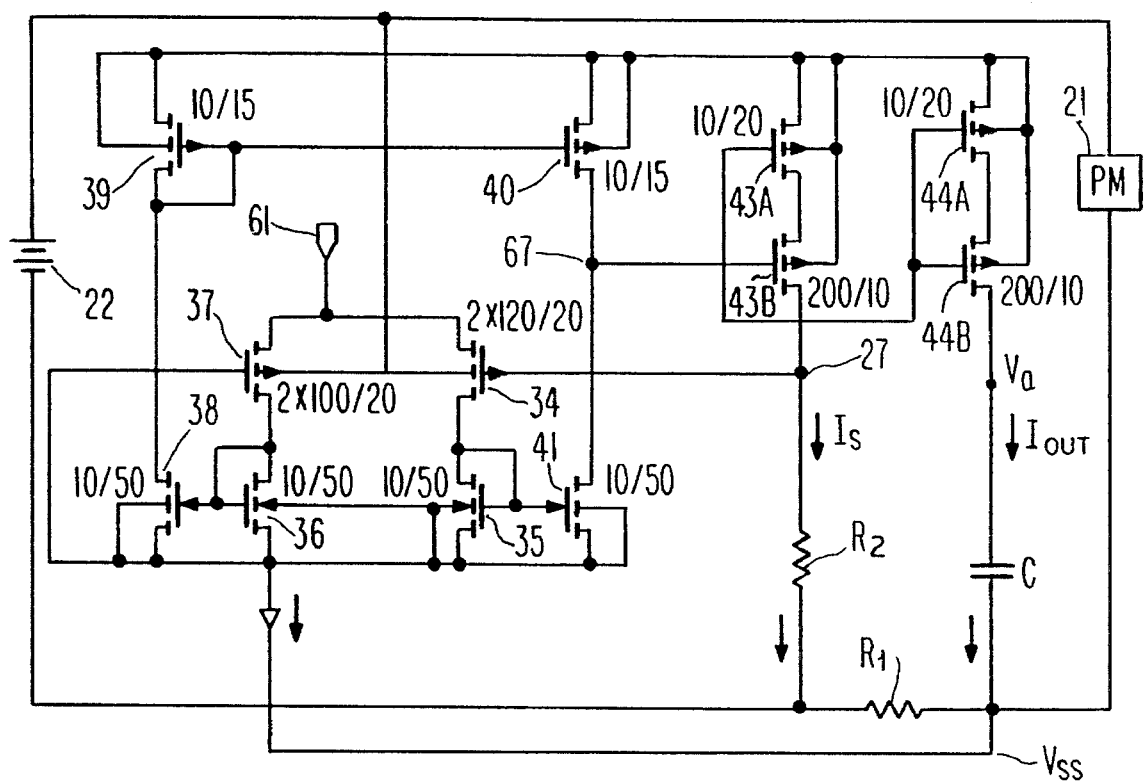
FIG. 4 is a more detailed circuit diagram of the input stage for providing a signal representative of pacemaker current.

Referring now to FIGS. 3 and 4, the input circuit will be described. In FIG. 3, a simplified diagram showing the feedback arrangement is provided. The input stage 25 is the most critical stage of the EOL detection subsystem. The main task of the input stage is to deliver a charging current for the capacitor C which is proportional to the line current $I_l$. While the minimal line current for a typical pacemaker is about 5 µA, suggesting a high value of resistance $R_1$, the value of $R_1$ is limited by the fact that at large line currents the voltage over the pacemaker circuitry drops with the value of the voltage across $R_1$. This forces the compromise discussed above. The feedback configuration of FIG. 3 includes a transistor 32 (pmos) in its feedback loop, to provide the relationship $I_s = R_1/R_2 \times I_l$. Referring to the detailed circuit diagram of FIG. 4, the input signal is developed at node 27, as also seen in FIG. 2. This signal is inputted into an operational amplifier comprising transistors 34–41, having an output at the node indicated at 67. The feedback for the operational amplifier (corresponding to single transistor 32 shown in FIG. 3) is provided by the combination of transistors 43A and 43B. The output current, designated $I_{out}$ is set equal to the input current $(I_s)$ by a current mirror circuit which includes transistors 44A and 44B, which are driven in a current mirror configuration with transistors 43A and 43B. Thus, the circuit provides a current proportional to $I_l$ into capacitor C. A bias port from bias block 61 is used to input the bias stage with a predetermined current.

FIG. 4 shows, for each of the transistors, the W/L ratio. The W/L ratios can affect the phase, gain, etc. and are important in the pacemaker embodiment for minimizing current drain. The design shown is illustrative, and not critical, and variations are well within the skill of a routine design engineer for providing a circuit with low current drain. Transistor 37 is indicated as 2*100/20, and transistor 34 is indicated as 2*120/20, each representing two transistors in parallel. The respective transistors 34, 37 are unbalanced in order to provide a built-in offset.

Figure 5A:
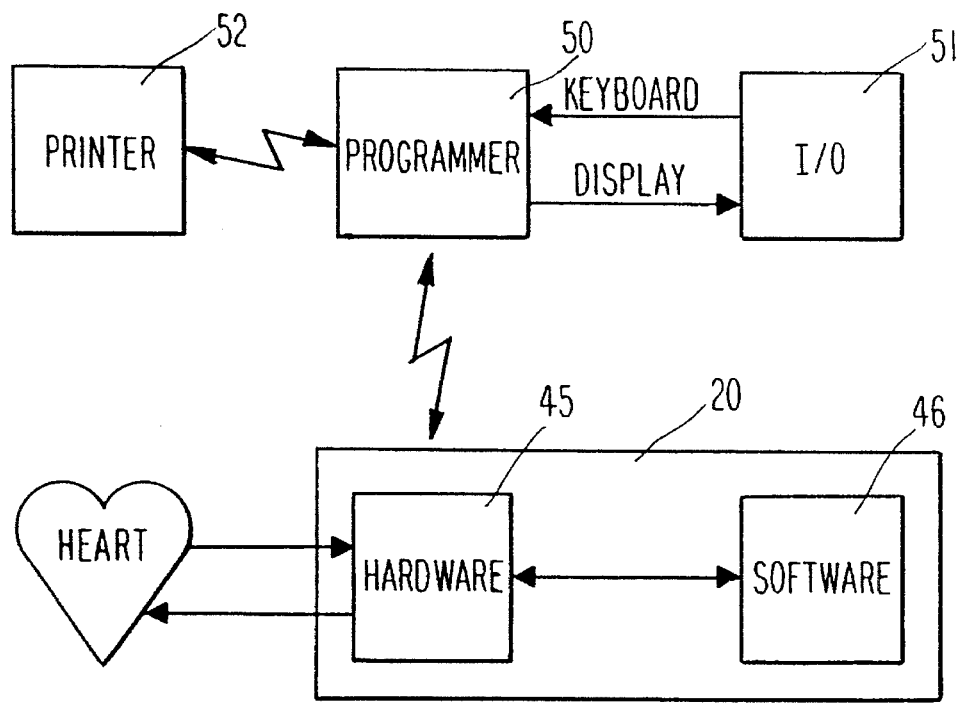
FIG. 5A is a simplified block diagram showing the pacemaker system of this invention, comprising the implanted pacemaker and external apparatus which has the capacity to communicate with the implanted pacemaker.
Figure 5B:
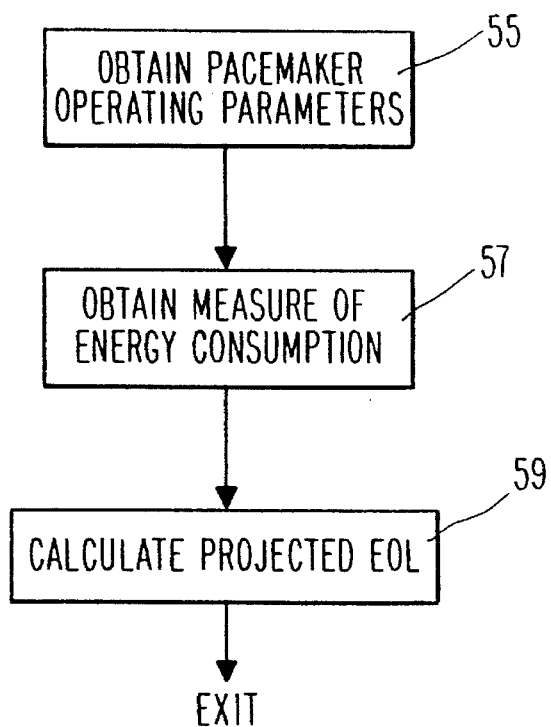
FIG. 5B shows a simplified flow diagram for calculating projected EOL of the implanted pacemaker.

Referring now to FIGS. 5A and 5B, there are shown further features of the overall pacemaker of this invention, having a subsystem for indicating EOL. As indicated in FIG. 5A, pacemaker 20 may incorporate both hardware 45 and software 46, in a known fashion. The hardware has circuitry for delivering stimulus pulses and receiving signals representative of natural heartbeats and other information from the heart. The software may be stored in the memory section of a processor chip, and may include additional RAM and ROM. The hardware 45 also interacts with an external programmer 50, in a known fashion. Programmer 50 interfaces with an input/output device (I/O) 51, such as a keyboard and/or display, and may also interface with a printer 52. Programmer 50 may be used to program the pacemaker, and also may be used in this system for enabling a physician to make precise determinations of EOL. Programmer 50 may suitably carry out the processing steps shown in FIG. 5B. As there illustrated, at step 55, the programmer interrogates the pacemaker and obtains current pacemaker operating parameters, i.e., voltage and duration of the pulse, pacing rate, etc. At step 57, the programmer reads out from pacemaker storage a measure of the energy consumption, as stored at counter 60 in the pacemaker. At step 59, the programmer calculates projected EOL. This includes determining battery capacity which is pre-stored in memory, substracting the energy consumption, and projecting the amount of time the pacemaker would operate at the present operating parameters to consume the remaining battery energy to the point of EOL. It is to be noted that, alternately, these operations may in fact be carried out in the implanted pacemaker, either automatically or on command from an external programmer, following which the projected EOL is read out by the physician, or some automatic indication is given to the patient.

Figure 6:
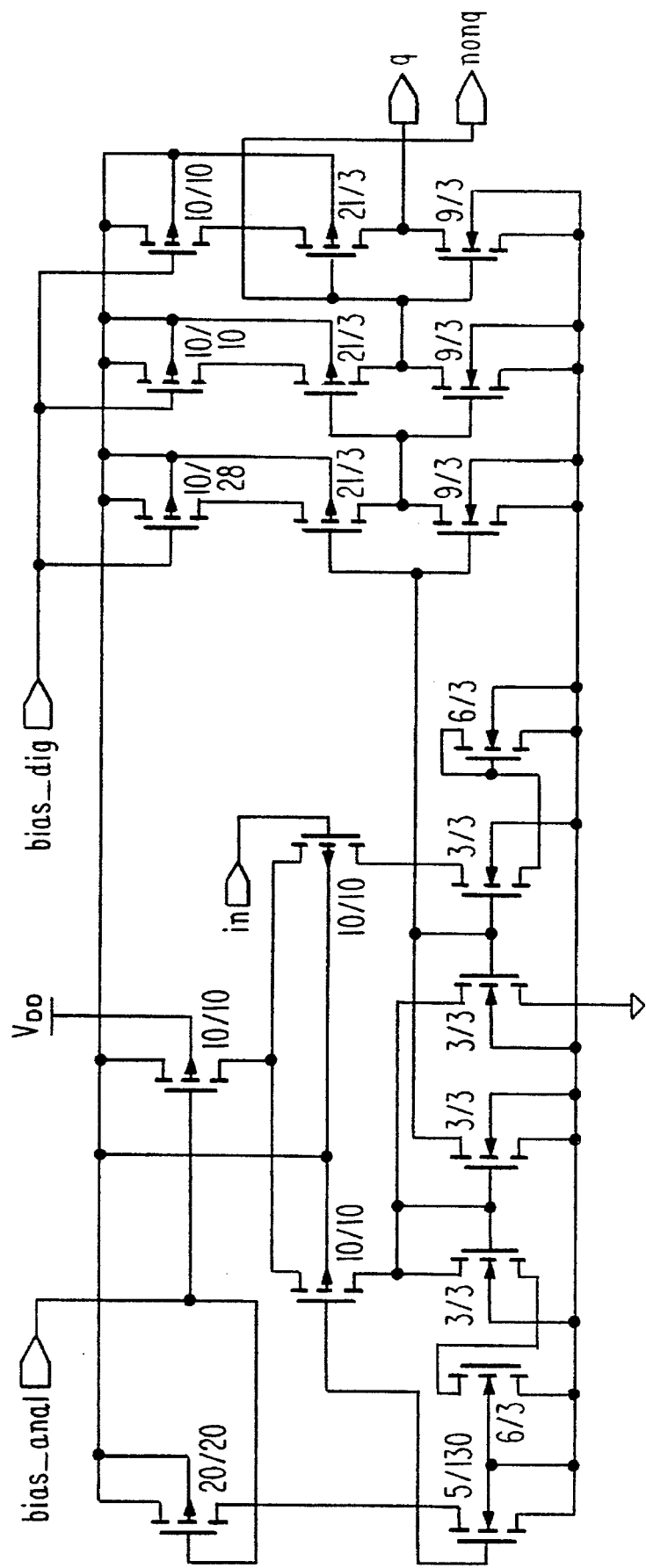
FIG. 6 is a circuit of a Schmitt Trigger suitable for use in the implantable pacemaker embodiment of this invention.

There has thus been disclosed an efficient and accurate subsystem for determining a measure of EOL in an implanted pacemaker. The configuration of the circuit results in a determination which is effectively independent of the capacitor which is used, thereby significantly enhancing accuracy of the EOL determination. While a specific circuit for the input stage has been illustrated, the other circuits are a matter of design choice, it being understood that for a pacemaker embodiment a low current drain is desirable. Thus, the Schmitt trigger 28, the AND circuit 31, the counter 60 and the bias block 61 may be conventional circuits which are well known in the art. Indeed, accuracy does not depend on the threshold of the Schmitt trigger. Of course, a relatively sophisticated design may be desired for a pacemaker, where long-term reliability and low energy consumption are desired. For an implantable pacemaker, the circuit should be very low power drain, and have good accuracy and a high slew-rate. The embodiment of FIG. 6 is representative of a preferred Schmitt Trigger. Variations of the overall circuit arrangement, for achieving substantially the same EOL result in substantially the same way, are within the scope of the invention.

While the preferred embodiment of the invention has been described as an implantable pacemaker, it is evident that the invention can be used in any device where battery depletion and EOL are important, and some automatic means of determining and indicating EOL is desirable. Thus, the invention is useful for other implantable medical devices, and for any battery-driven device where accuracy of detecting EOL is important.

What is claimed is:

1. A pacemaker having a battery, pacemaker circuitry for carrying out pacing functions, and an energy consumption detector, said detector comprising (a) accumulating means for accumulating a signal representative of the integral of pacemaker circuitry current over the time since it last started to accumulate said signal;

(b) readout means for reading out said accumulated signal when it reaches a predetermined threshold and for developing therefrom a measure of battery expenditure over said time;

(c) said readout means having means for zeroing out said accumulated signal so that said accumulating means repeats the function of accumulating a said representative signal from the time of said zeroing out until the time of the next readout; and (d) means for accumulating signals which have been read out and for storing a signal representative of overall battery expenditure.

2. The pacemaker as described in claim 1, wherein said accumulating means comprises sense means for continuously sensing a measure of current flow through said pacemaker circuitry.

3. The pacemaker as described in claim 1, wherein said accumulating means comprises a capacitor and charging means for charging said capacitor with a current proportional to said pacemaker circuitry current.

4. The pacemaker as described in claim 3, wherein said readout means comprises means for discharging said capacitor to a predetermined value and for developing a series of pulses during the time of discharge of said capacitor, said series of pulses representing a measure of the energy discharged from said capacitor.

5. The pacemaker as described in claim 4, wherein said readout means comprises means for initiating readout of said capacitor when the voltage on said capacitor reaches a first threshold, and means for terminating readout of said capacitor when the voltage on said capacitor reaches a second threshold.

6. The pacemaker as described in claim 3, wherein said readout means comprises discharge means for discharging said capacitor at a constant discharge current.

7. The pacemaker as described in claim 1, wherein said accumulating means comprises a current sense means for sensing the pacemaker circuitry current, in combination with a circuit for providing a current having a predetermined linear relation to said sensed current.

8. The pacemaker as described in claim 1, in combination with means for inputting pacemaker operating parameter data, means for obtaining from said operating data an estimate of the rate at which said pacemaker is currently using energy from said battery, and means for determining a measure of end of life of said pacemaker from said estimate and from said stored signal representative of overall battery expenditure.

9. An implantable pacemaker system having a battery for the supply of energy, a pacing subsystem connected to said battery for generating and delivering pacing pulses to a patient, and a circuit for obtaining a measure of battery discharge, said circuit comprising, sense means for generating a current proportional to the current through said pacemaker subsystem;

a capacitor connected to receive said proportional current;

discharge means for cyclically discharging said capacitor;

measure means for determining a measure of the energy discharged from said capacitor each time it is discharged and for generating signals representative of said measure, said signals thus being representative of battery discharge during each charging of said capacitor; and accumulating means for accumulating said representative signals, thereby providing a measure of overall battery discharge.

10. The pacemaker as described in claim 9, wherein said discharge means comprises a trigger circuit which triggers when the voltage on said capacitor rises to a predetermined level.

11. The pacemaker as described in claim 9, wherein said discharge means comprises means for discharging said capacitor at a constant discharge current.

12. The pacemaker as described in claim 11, wherein said measure means comprises a pulse generator having a period between pulses much greater than the time of discharge of said capacitor, and count means for counting said pulses during said time of discharge.

13. An implantable pacemaker system having a battery for the supply of energy, a pacing subsystem powered by said battery for generating and delivering pacing pulses to a patient, and a circuit for obtaining a measure of the energy discharge of said battery, said circuit comprising:

a) a sense circuit for sensing current through said pacemaker circuitry, a capacitor and a charging circuit connecting said sense circuit and said capacitor for charging said capacitor with a charge which is a measure of the integral of said sensed current over time, and thus of battery energy discharge while said capacitor is charging;

b) discharge means for discharging said capacitor at a fixed discharge current, whereby the time of discharge is a measure of said integral and independent of the value of said capacitor; and c) a measuring circuit for developing a representative signal representative of said discharge time and thus representative of said integral.

14. The pacemaker system as described in claim 13, further comprising cycle means to continuously enable said charging and said discharging, and means to accumulate said representative signals, thereby providing a measure of overall battery discharge.

15. A device having a battery for the supply of energy, a subsystem connected to said battery for performing predetermined functions, and a circuit for obtaining a measure of battery discharge, said circuit comprising, sense means for generating a current proportional to the current through said subsystem;

a capacitor connected to receive said proportional current;

discharge means for cyclically discharging said capacitor at a constant discharge current;

signal means for generating signals representative of the energy discharged from said capacitor each time it is discharged, said signals thus being representative of battery discharge during each charging of said capacitor; and accumulating means for accumulating said representative signals, thereby providing a measure of overall battery discharge.

16. The device as described in claim 15, wherein said signal means comprises a pulse generator having a pulse rate with a period which is short relative to the time of discharge of said capacitor.

17. The device as described in claim 16, wherein said pulse generator has a rate in the range of about 500 Hz to 5000 Hz.

* * * * *